United States Patent
Pan et al.

(10) Patent No.: US 8,378,302 B2
(45) Date of Patent: Feb. 19, 2013

(54) BIDIRECTIONAL OPTICAL SCANNER ASSISTING IN MAMMOGRAPHY

(75) Inventors: Min-Chun Pan, Pingzhen (TW);
Hung-Chin Chiang, Chiayi (TW);
Chun-Yu Chen, Banqiao (TW);
Liang-Yu Chen, Taoyuan (TW);
Ching-Tang Wu, Taoyuan (TW);
Min-Cheng Pan, Keelung (TW)

(73) Assignee: National Central University, Jhongli, Taoyuan County (TW)

( * ) Notice: Subject to any disclaimer, the term of this patent is extended or adjusted under 35 U.S.C. 154(b) by 63 days.

(21) Appl. No.: 13/035,287

(22) Filed: Feb. 25, 2011

(65) Prior Publication Data
US 2012/0085908 A1    Apr. 12, 2012

(30) Foreign Application Priority Data
Oct. 11, 2010  (TW) .............................. 99134522 A

(51) Int. Cl.
*G01J 5/02*     (2006.01)
(52) U.S. Cl. .............................. 250/339.02; 250/370.08
(58) Field of Classification Search ............. 250/370.08, 250/339.02
See application file for complete search history.

(56) References Cited

U.S. PATENT DOCUMENTS

| | | | | |
|---|---|---|---|---|
| 4,515,165 | A * | 5/1985 | Carroll | 600/475 |
| 5,999,836 | A * | 12/1999 | Nelson et al. | 600/407 |
| 2008/0218727 | A1* | 9/2008 | Djeziri et al. | 356/2 |
| 2009/0005692 | A1* | 1/2009 | Intes et al. | 600/477 |
| 2010/0246759 | A1* | 9/2010 | Ogura et al. | 378/21 |

OTHER PUBLICATIONS

Chen, J.Y. et al., "Breast Tumor Detection Instrument Through Mammography Based NIR Dot", Proceedings of the 2010 Design of Medical Devices Conference, Apr. 13-15, 2010, pp. 1-4, Minneapolis, MN.

* cited by examiner

*Primary Examiner* — Marcus Taningco
(74) *Attorney, Agent, or Firm* — Muncy, Geissler, Olds & Lowe, PLLC

(57) ABSTRACT

A bidirectional optical scanner assisting in mammography is revealed. The optical scanner that calculates functional images obtained by diffuse optical tomography, used in combination with a mammography machine can reduce the number of mammograms taken and the dose exposure. The bidirectional optical scanner includes a compression module, a first optical detection module, and a second optical detection module. The same test position of the tested breast can be detected twice in different directions by the first and the second optical detection modules. No matter where the tumor is located, the tumor can be detected. Besides structural images provided by the mammography machine, functional tomographic images of the breast are obtained by the bidirectional optical scanner. Thus diagnostic accuracy in the detection of breast cancer is improved.

23 Claims, 7 Drawing Sheets

BIDIRECTIONAL OPTICAL SCANNER ASSISTING IN MAMMOGRAPHY

BACKGROUND OF THE INVENTION

1. Fields of the Invention

The present invention relates to a bidirectional optical scanner, especially to a bidirectional optical scanner assisting in mammography with improved accuracy of breast cancer diagnosis.

2. Descriptions of Related Art

Breast cancer, the most common cancer in women, caused 500,000 deaths per year worldwide. In western countries, breast cancer afflicts 25 percent of all female cancer patients. According to a medical paper published in Taiwan 2003, breast cancer is the fourth most common cause of female cancer death.

The peak age of breast cancer in oriental women is around 40-50 years old, while that in the western countries is around 30-40. Compared with other cancers, breast cancer is easier to be detected at an early stage. When people feel a lump in the breast, some are reluctant to acknowledge the presence and afraid to have surgery. Thus they tend to delay the treatment. In fact, most breast lumps are benign and many choices are available for the treatment of breast cancer beside removal of the whole breast. In recent clinical practice, the average 10-year disease-free survival rate is 60%. The average 10-year breast cancer survival rate for stage 1 breast cancer with best treatment is 80%. Treatment for stage 0 breast cancer is very successful and the survival rate for stage 0 is nearly 100%. Therefore, early detection and treatment of breast cancer are very important.

Self-examination and doctor's touch are both regular examinations of women's breasts to detect breast cancer earlier. Once abnormal changes are observed, further image analysis is required. The medical ultrasonic Imaging system and mammography are used as diagnostic and screening tools for detecting early breast cancer. They are also used as criterions while making comparison with other breast imaging techniques. In routine examinations, medical ultrasonic Imaging is used for first visit due to the properties of real-time imaging and low cost. As to the mammography, it is a useful screening tool because it detects micro-calcification clusters with high sensitivity and the lesion is detected earlier. Another technique-magnetic resonance imaging (MRI), the widespread of this technique is limited by the high cost of the instrument and the exam. Yet the image resolution of the MRI is higher than the above two techniques and the MRI provides functional imaging.

Like other X-ray tests, mammography uses low-dose ionizing radiation to penetrate the body and create an image. The image is analyzed by radiologists. However, mammography has encountered opposition from the medical professionals due to the high false rate and the radiation does during the test. The false-negative rate of the mammography is at least 10%. The false-negative means a result that appears negative but fails to reveal a condition of having cancer. This is due to dense tissues obscuring the small tumor and the fact that the appearance of cancer on mammograms has a large overlap with the appearance of normal tissues. Some other women are given a false-positive (showing abnormalities, but not cancer) mammogram result.

In order to solve the above problems, there is a need to provide a device assisting in mammography for fewer mammograms and reducing dose exposure.

SUMMARY OF THE INVENTION

Therefore it is a primary object of the present invention to provide a bidirectional optical scanner used as an aid in mammography for reducing the number of mammograms taken and lowering the dose exposure.

It is another object of the present invention to provide a bidirectional optical scanner that detects the same test position of a tested breast twice in two directions. Thus the breast cancer can be detected no matter where it is located. Moreover, besides conventional structural images provided by mammography, the present invention provides functional tomographic images of the tested breast so as to enhance the diagnostic accuracy of breast cancer.

It is a further object of the present invention to provide a bidirectional optical scanner that detects breast cancer over a large area with improved detection speed and reduced detection time.

It is a further object of the present invention to provide a bidirectional optical scanner that is moveable to get images, not limited by the shape of the tested breast. Thus the bidirectional optical scanner can detect tumor cells in different shapes of breast.

In order to achieve above objects, the bidirectional optical scanner of the present invention consists of a compression module having a first compression plate and a second compression plate, a first optical detection module disposed over the first compression plate, and a second optical detection module arranged under the second compression plate. The first optical detection module includes at least one light source module and at least one detection module. The light source module is formed by a plurality of light emitting elements arranged in a line. The detection module is composed of a plurality of photosensors set in a line. One of the light emitting elements is aligned with corresponding photosensor to form a row. The second optical detection module also includes at least one light source module and at least one detection module. The light source module having a plurality of light emitting elements arranged in a line while the detection module includes a plurality of photosensors set in a line. Each light emitting elements is aligned with corresponding photosensor to form a row. The light emitting elements of the light source module of the second optical detection module are corresponding to the photosensors of the detection module of the first optical detection module. The photosensors of the detection module of the second optical detection module are corresponding to the light emitting elements of the light source module of the first optical detection module.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENT

Figure 1:
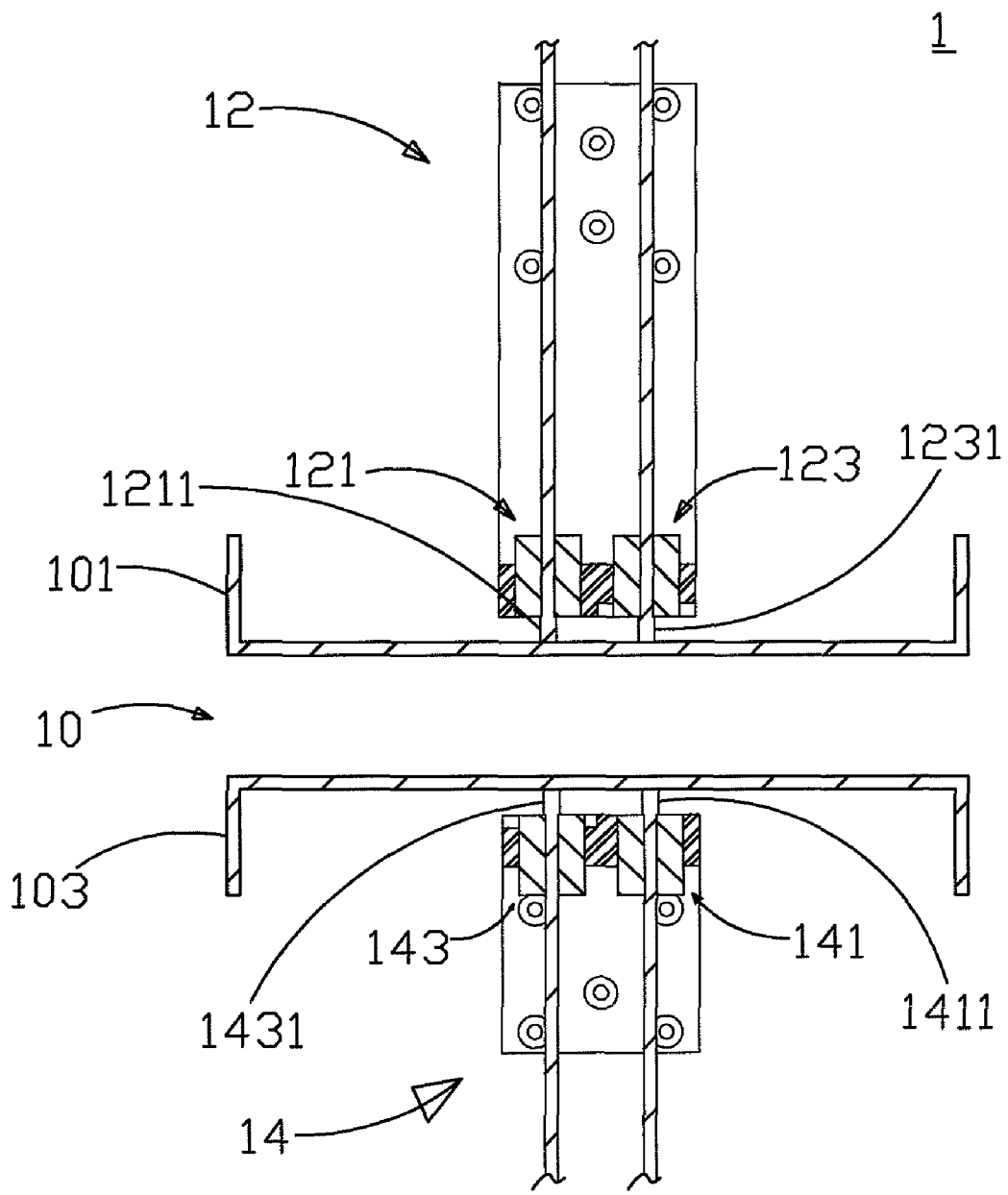
FIG. 1 is a cross sectional view of an embodiment according to the present invention.

Refer to FIG. 1, a cross sectional view of a bidirectional optical scanner 1 is revealed. The bidirectional optical scanner 1 used for breast cancer diagnosis includes a compression module 10, a first optical detection module 12, and a second optical detection module 14. The compression module 10 consists of a first compression plate 101 and a second compression plate 103 while the first compression plate 101 is disposed over the second compression plate 103. The first compression plate 101 and the second compression plate 103 are used for pressing a breast to be detected for convenience of performing tests.

Figure 2:
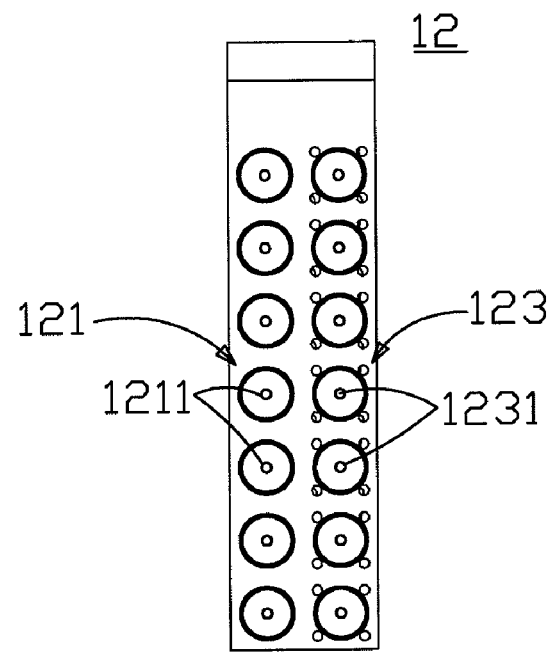
FIG. 2 is a schematic drawing showing an embodiment of a first optical detection module according to the present invention.

The first optical detection module 12 is disposed over the first compression plate 101. Also refer to FIG. 2, a schematic drawing showing an embodiment of the first optical detection module 12 is revealed. The first optical detection module 12 consists of a light source module 121 and a detection module 123. The light source module 121 is composed of a plurality of light emitting elements 1211 arranged in a line. Each light emitting element 1211 is an optical fiber that emits laser light or broadband light. The wavelength of the laser light or the broadband light is near infrared wavelength.

The detection module 123 includes a plurality of photosensors 1231 arranged in a line and each photosensor 1231 is an optical fiber. The optical fiber generates an optical signal and the optical signal is sent to a signal processing module. The light emitting elements 1211 of the light source module 121 and the photosensors 1231 of the detection module 123 are arranged in an array. The light emitting elements 1211 and the photosensors 1231 respectively are arranged in a line and each light emitting element 1211 is aligned with the corresponding photosensor 1231 to form a row.

Figure 3:
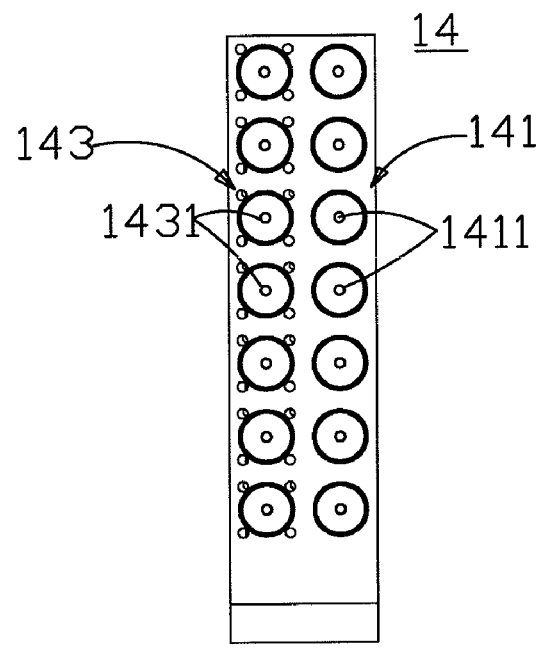
FIG. 3 is a schematic drawing showing an embodiment of a second optical detection module according to the present invention.

Refer to FIG. 3, a schematic drawing showing an embodiment of a second optical detection module 14 is disclosed. As shown in figure, the second optical detection module 14 is disposed under the second compression plate 103. The second optical detection module 14 also includes a light source module 141 and a detection module 143. The light source module 141 consists of a plurality of light emitting elements 1411 and each light emitting element 1411 is an optical fiber that emits laser light or broadband light. The wavelength of the laser light or broadband light is near infrared wavelength. The detection module 143 includes a plurality of photosensors 1431 and each photosensor 1431 is an optical fiber. The optical fiber generates an optical signal and the optical signal is sent to a signal processing module. The light emitting elements 1411 of the light source module 141 and the photosensors 1431 of the detection module 143 are arranged in an array. The light emitting elements 1411 and the photosensors 1431 respectively are arranged in a line and each light emitting element 1411 is aligned with the corresponding photosensor 1431 to form a row.

The light source module 141 of this embodiment is corresponding to the detection module 123 of the first optical detection module 12. Each light emitting element 1411 of the light source module 141 is corresponding to each photosensor 1231 of the detection module 123. Similarly, the detection module 143 is corresponding to the light source module 121 of the first optical detection module 12. Each photosensor 1431 of the detection module 143 is corresponding to each light emitting element 1211 of the light source module 121. Thus the number of the light emitting element 1211 of the light source module 121 of the first optical detection module 12 is equal to the number of the photosensor 1431 of the detection module 143 of the second optical detection module 14. The number of the photosensor 1231 of the detection module 123 of the first optical detection module 12 is equal to the number of the light emitting element 1411 of the light source module 141 of the second optical detection module 14. The larger the number of the light emitting element 1211, 1411 of the light source module 121, 141 of the first and the second optical detection modules 12, 14, and the photosensor 1231, 1431 of the detection modules 123, 143, the higher accuracy of diagnostic imaging of the bidirectional optical scanner 1 is.

Figure 4A:
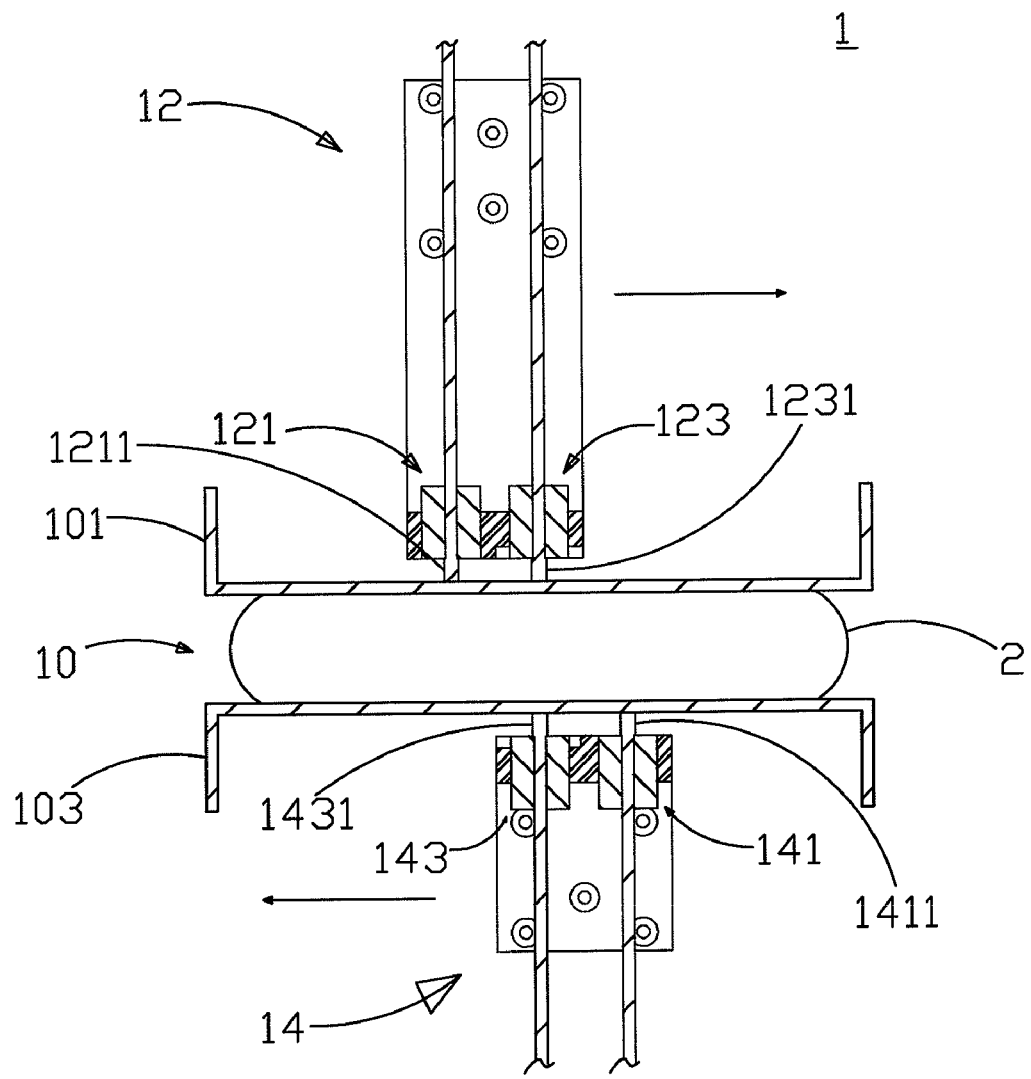
FIG. 4A and FIG. 4B are schematic drawings showing an embodiment in use according to the present invention.
Figure 4B:
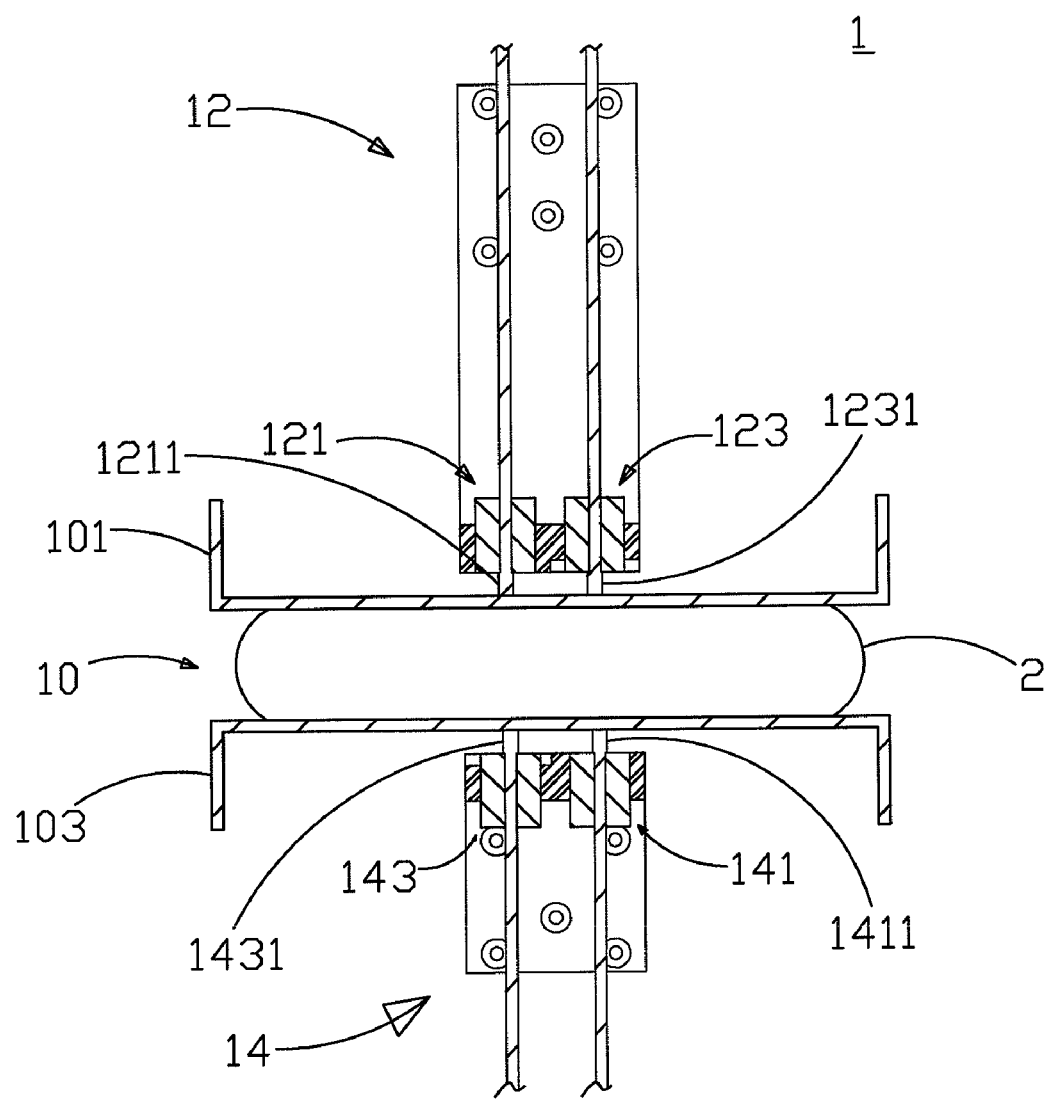

Refer to FIG. 4A and FIG. 4B, while taking breast images by the bidirectional optical scanner 1 of the present invention, one breast 2 to be tested of a patient is set on the second compression plate 103 of the compression module 10. Then the breast 2 set on the second compression plate 103 is compressed by the first compression plate 101 of the compression module 10 and the breast tissues is spread out evenly so that all of the tissue can be visualized.

Each light emitting element 1211 of the light source module 121 of the first optical detection module 12 emits light to a plurality of test positions on the tested breast 2 compressed by the compression module 10. The test positions are determined according to the light emitting elements 1211 of the light source module 121 and the photosensors 1231 of the detection modules 123 of the first optical detection module 12, and the light emitting elements 1411 of the light source module 141 and the photosensors 1431 of the detection module 143 of the second optical detection module 14. Each photosensor 1431 of the detection module 143 of the second optical detection module 14 receives photons from the corresponding test position and generates an optical signal. The optical signals from corresponding test positions are converted into a plurality of electrical signals and the electrical signals are sent to a signal processing module.

Refer to FIG. 4B, the first optical detection module 12 is shifted to the right side while the second optical detection module 14 is shifted to the left side. The light emitting elements 1411 of the light source module 141 of the second optical detection module 14 emit light to a plurality of test positions on the tested breast 2 compressed. Each photosensor 1231 of the detection module 123 of the first optical detection module 12 on the top receives photons from the corresponding test position and generates an optical signal. The optical signals from corresponding test positions are converted into a plurality of electrical signals and the electrical signals are sent to the signal processing module.

As shown in FIG. 4A, it is learned that the light emitting elements 1211 on the top side of the device emit light through the test positions over the corresponding test position and then photosensors 1431 on the bottom of the device receives photons from the corresponding test positions so as to generate electrical signals corresponding to the test positions. Thus the same test position has been detected twice. The light source on the top emits light to the test position for the first time while the other time, the light source on the bottom projects light through the test position. At last, the electrical signals obtained from the two tests are treated by functional optical image backward process so as to get a correct image of the test position. Then an image of the breast 2 with high resolution is obtained by reconstruction of the correct images of each test position. Therefore, whether there is a tumor inside the breast 2 is checked according to the image of the breast 2.

The tumor may be located at the upper part of the tested breast 2 or at the lower part of the tested breast 2. By the bidirectional optical scanner 1 of the present invention, each test position of the tested breast 2 has been detected two times in two directions. Thus either the tumor on the upper part of the tested breast 2 or the tumor on the lower part of the tested breast 2 can be detected. Compared with structural images provided by mammography, the present invention provides functional tomographic images of the breast so as to enhance the diagnostic accuracy of breast cancer.

Figure 5:
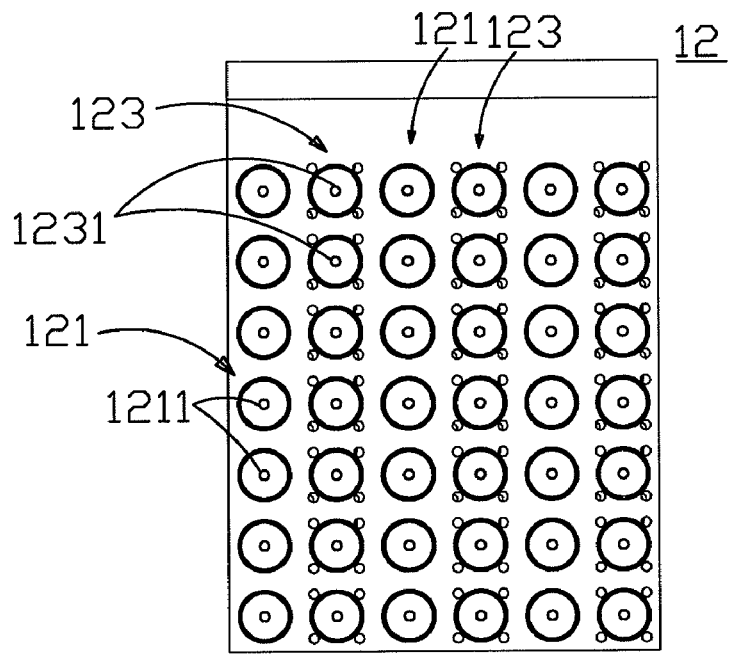
FIG. 5 is a schematic drawing showing another embodiment of a first optical detection module according to the present invention.
Figure 6:
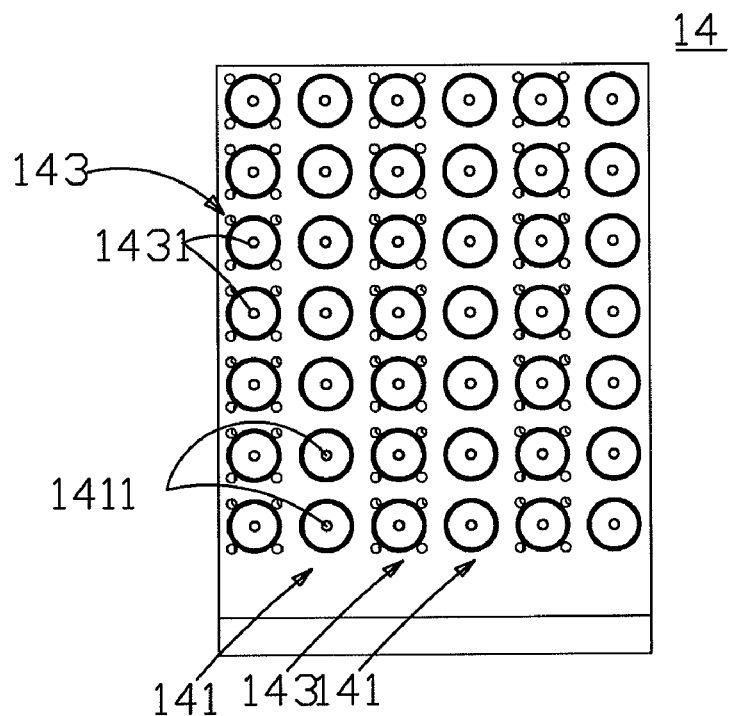
FIG. 6 is a schematic drawing showing another embodiment of a second optical detection module according to the present invention.

Refer to FIG. 5 and FIG. 6, schematic drawings showing another embodiment of the first optical detection module and another embodiment of the second optical detection module are revealed. In the above embodiment, the first optical detection module 12 and the second optical detection module 14 respectively only include one light source module 121, 141 and one detection module 123, 143. In this embodiment, in order to improve detection efficiency and reduce detection time, the first optical detection module 12 and the second optical detection module 14 respectively include a plurality of the light source modules 121, 141 and a plurality of detection modules 123, 143. The light source modules 121, 141 and the detection modules 123, 143 are arranged in turn.

Each light source module 121, 141 includes a plurality of light emitting elements 1211, 1411 arranged in a line. Each detection module 123, 143 consists of a plurality of photosensors 1231, 1431 and these photosensors 1231, 1431 are also disposed in a line. When the light source modules 121, 141 and the detection modules 123, 143 are arranged in turn, the light emitting elements 1211, 1411 of the light source modules 121, 141 together with the photosensors 1231, 1431 of the detection modules 123, 143 form an array. In each row of the first optical detection module 12, the light emitting elements 1211 and the photosensors 1231 are arranged alternatively. In similar way, the photosensors 1431 and the light emitting elements 1411 on each row of the second optical detection module 14 are arranged alternatively, in the order of the photosensor 1431, the light emitting element 1411, the photosensor 1431, etc.

Thus the first optical detection module 12 and the second optical detection module 14 are used for large area screening of breast cancer. All of the test positions on the tested breast 2 are detected at one time. Then the first optical detection module 12 and the second optical detection module 14 are moved horizontally so as to detect the test positions of the tested breast 2 once again. Therefore, the detection efficiency is improved and the detection time is reduced significantly.

Figure 7:
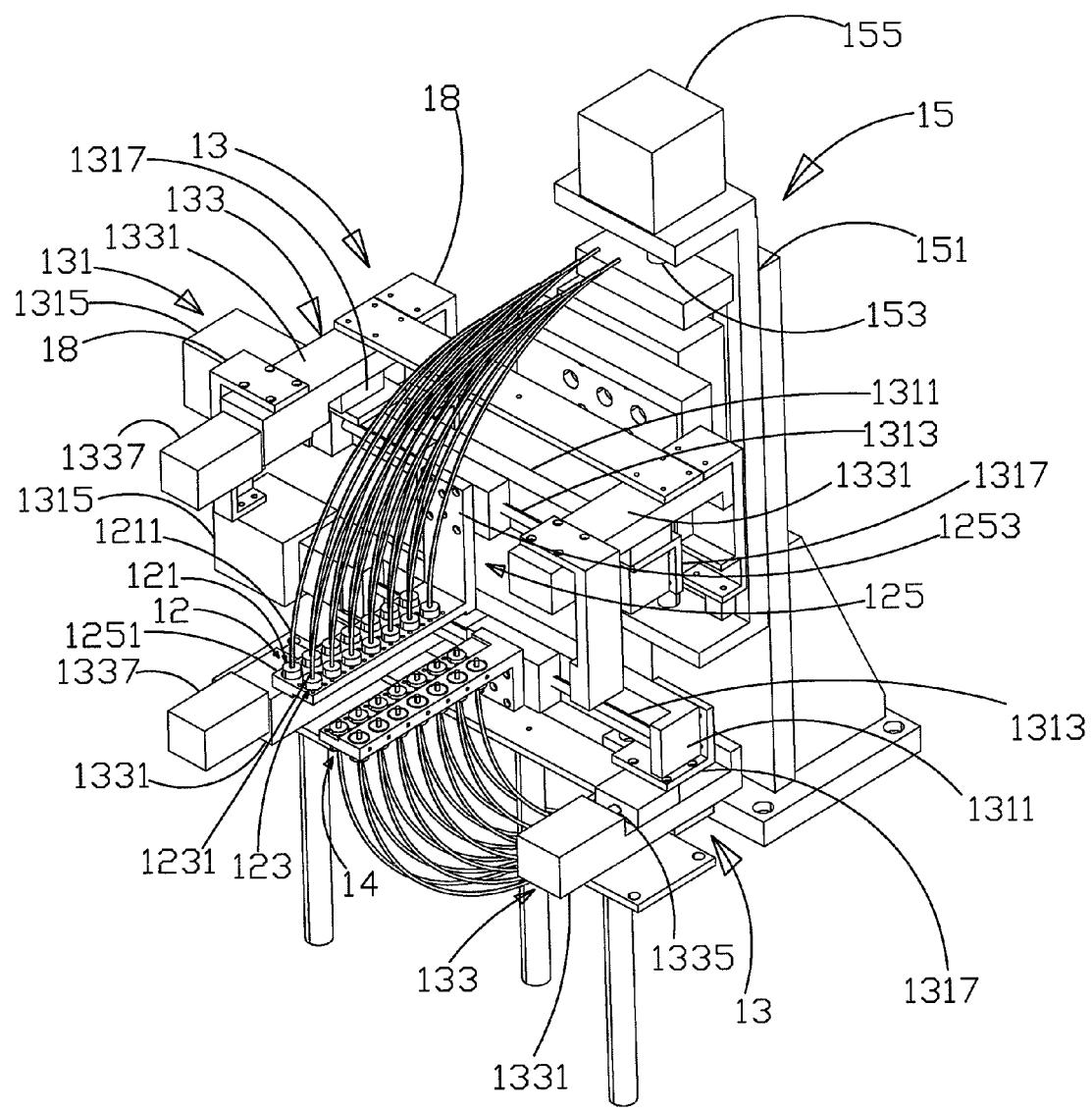
FIG. 7 is a perspective view of a further embodiment according to the present invention.
Figure 8:
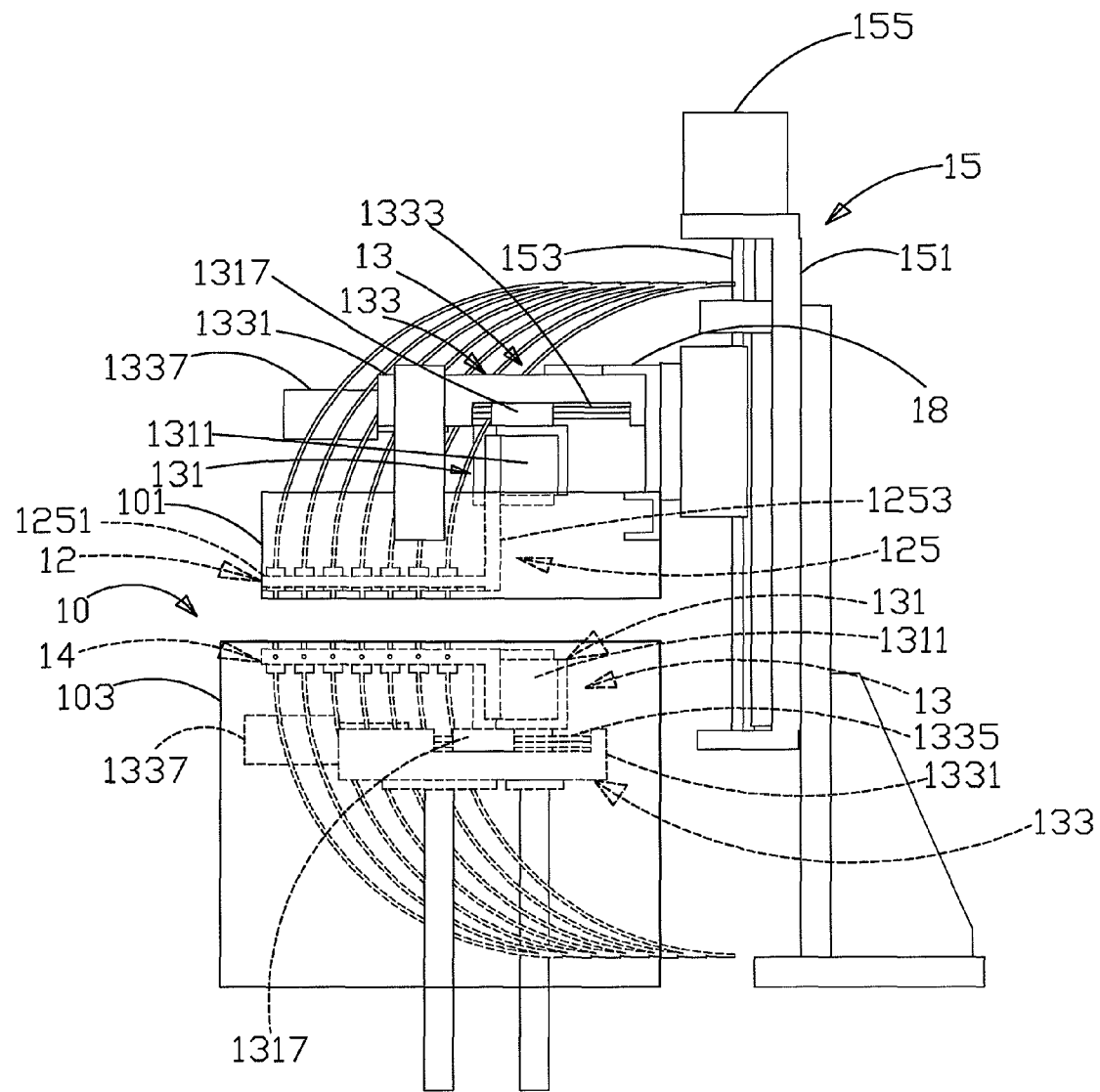
FIG. 8 is a side view of a further embodiment according to the present invention.

Refer to FIG. 7 and FIG. 8, a further embodiment of the present invention is revealed. From the above embodiments, it is learned that the first optical detection module 12 and the second optical detection module 14 should be moved horizontally in order to detect each test position on the tested breast twice. The first optical detection module 12 and the second optical detection module 14 respectively are arranged at a corresponding moving platform 13. The moving platform 13 is mainly used to drive the first optical detection module 12 or the second optical detection module 14 moving in both the X-direction and the Y-direction.

Take the first optical detection module 12 set on the moving platform 13 as an example. The moving platform 13 includes a first moving platform 131 and a second moving platform 133. The first optical detection module 12 (or the second optical detection module 14) is disposed on the first moving platform 131. The first moving platform 131 drives the first optical detection module 12 (or the second optical detection module 14) to move in the X-direction (left and right movement). The first moving platform 131 arranged with the first optical detection module 12 (or the second optical detection module 14) is disposed on the second moving platform 133. The second moving platform 133 drives the first optical detection module 12 on the first moving platform 131 moving in the Y-direction (forward and backward movement). Thus the position of the first optical detection module 12 (or the second optical detection module 14) is adjusted by the moving platform 13 according to the shape of the breast compressed by the compression module 10. Thus this embodiment of the bidirectional optical scanner 1 is not restricted by the shape of the compressed breast in the breast cancer detection, still obtaining a good breast image.

The first moving platform 131 consists of a base 1311, a threaded rod 1313, and a driving device 1315. The threaded rod 1313 and the driving device 1315 are arranged at the base 1311. The driving device 1315 is connected to the threaded rod 1313 while the first optical detection module 12 (or the second optical detection module 14) is screwed on the threaded rod 1313. The driving device 1315 is a servo motor. When the driving device 1315 drives the threaded rod 1313 rotating, the threaded rod 1313 moves the first optical detection module 12 (or the second optical detection module 14) in the X-direction therealong.

Moreover, the first optical detection module 12 (or the second optical detection module 14) is connected to the threaded rod 1313 of the first moving platform 131 by a fastener 125. The fastener 125 is L-shaped and having a first fixed end 1251 and a second fixed end 1253. The light source modules 121 and the detection modules 123 of the first optical detection module 12 are fixed on the first fixed end 1251 of the fastener 125. In the above embodiment, the first optical detection module 12 is disposed on the first moving platform 131 of the moving platform 13. The second optical detection module 14 is arranged at the first moving platform 131 in a similar way.

The second moving platform 133 and the first moving platform 131 are perpendicular to each other. As shown in FIG. 8, the second moving platform 133 corresponding to the first optical detection module 12 is located over the first moving platform 131 corresponding to the first optical detection module 12. The second moving platform 133 corresponding to the second optical detection module 14 is located under the first moving platform 131 corresponding to the second optical detection module 14.

Refer to FIG. 7 and FIG. 8, how the second moving platform 133 corresponding to the first optical detection module 12, and the first moving platform 131 corresponding to the first optical detection module 12 are connected to each other is described in the following. The second moving platform 133 is composed of a base 1331, a first threaded rod 1333, a second threaded rod 1335 and a driving device 1337. The base 1331 is over the first moving platform 131 and is perpendicular to the base 1311. The first threaded rod 1333 and the second threaded rod 1335 respectively are set on each of two sides of the base 1331. The driving device 1337 is disposed on the base 1331 and is connected to the first threaded rod 1333. The first moving platform 131 is set on the first threaded rod 1333 and the second threaded rod 1335. When the driving device 1337 drives the first threaded rod 1333 to rotate, the first threaded rod 1333 further drives the first moving platform 131 with the first optical detection module 12 to move and drive the second threaded rod 1335. Thus the first threaded rod 1333 together with the second threaded rod 1335 makes the first moving platform 131 move steadily in the Y-direction therealong. Therefore, the first optical detection module 12 arranged at the first moving platform 131 also moves along with the first moving platform 131, having displacement in the Y-direction.

The first moving platform 131 and the second moving platform 133 are connected with each other by two connection parts 1317. One end of the connection parts 1317 is fixed on the base 1311 of the first moving platform 131 while the other end of the connection parts 1317 is screwed on the first threaded rod 1333 and on the second threaded rod 1335. The above is the way the second moving platform 133 connected to the first moving platform 131 with the first optical detection module 12. The first moving platform 131 disposed with the second optical detection module 14 is also connected to the corresponding second moving platform 133 in the similar way.

Both the first optical detection module 12 and the second optical detection module 14 of this embodiment move in the X-direction and the Y-direction through the first moving platform 131 and the second moving platform 133 of the moving platform 13. Thus the bidirectional optical scanner 1 in this embodiment including the moveable first optical detection module 12 and the moveable second optical detection module 14 is not limited by the shape of the breast compressed between the first compression plate 101 and the second compression plate 103 of the compression module 10, producing a good image of breast.

Still refer to FIG. 7 and FIG. 8, the displacement of both the first optical detection module 12 and the second optical detection module 14 in the X-direction and the Y-direction are controlled by the moving platform 13. The bidirectional optical scanner 1 further includes a third moving platform 15 that controls the displacement of the first optical detection module 12 and the first compression plate 101 of the compression module 10. While taking a breast image by the bidirectional optical scanner 1, the breast is compressed firstly by the compression module 10. The tested breast is set on the still second compression plate 103 while the first compression plate 101 is moved downward to compress the tested breast. Thus the third moving platform 15 of this embodiment is used to control the movement of the first compression plate 101. Moreover, the first optical detection module 12 is disposed over the first compression plate 101. While moving the first compression plate 101, the first optical detection module 12 needs to be moved firstly. Thus when the first compression plate 101 is moved upward, the third moving platform 15 drives both the first compression plate 101 and the first optical detection module 12 to move upward. On the other hand, the first optical detection module 12 is also moved downward by the third moving platform 15 along with the first compression plate 101 while the first compression plate 101 moving downward.

The third moving platform 15 is composed of a base 151, a threaded rod 153, and a driving device 155. The threaded rod 153 and the driving device 155 are disposed on the base 151. The driving device 155 is connected to the threaded rod 153 while the first optical detection module 12 and first compression plate 101 are screwed on the threaded rod 153 of the third moving platform 15 through a frame 18. Both the first compression plate 101 of the compression module 10 and the second moving platform 133 connected to the first moving platform 131 are fixed on the frame 18. And the frame 18 is screwed on the threaded rod 153. When the driving device 155 drives the threaded rod 153 to rotate, the threaded rod 153 moves the frame 18 in the Z-direction. The moved frame 18 further drives the first compression plate 101 and the first optical detection module 12 to move in the Z-direction.

The bidirectional optical scanner 1 of this embodiment can be arranged at a mammography machine. Generally, the mammography machine already includes a lifting mechanism so that the third moving platform 15 can be replaced by the lifting mechanism of the mammography machine. While shooting the image, both a mammogram image and a breast image are taken at the same time by the mammography machine and the bidirectional optical scanner 1 of the present invention. Then the obtained images are compared so as to improve accuracy of breast cancer imaging.

In summary, the bidirectional optical scanner of the present invention detects the same test position of the tested breast twice in different directions. No matter where the tumor is located, it can be detected. Compared with structural images provided by conventional mammography, the present invention provides functional tomographic images of the breast so that diagnostic accuracy in the detection of breast cancer is improved.

Moreover, the higher the number of the light emitting elements of the light source module and the photosensors of the detection module of the first and the second optical detection modules, the denser the test positions of the tested breast. Thus the breast cancer diagnosis is more accurate.

Furthermore, the light emitting elements of the light source module and the photosensors of the detection module of the first and the second optical detection modules are arranged into an array for large-area detection, quick detection and reduced detection time.

In addition, the first and the second optical detection modules of the present invention are respectively disposed on a corresponding moving platform. Each moving platform controls the displacement of one optical detection module in the X-direction and in the Y-direction. Thus the image shooting is not affected by the shape of the tested breast. Thus the bidirectional optical scanner of the present invention is applied to breasts having various shapes for cancer detection.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A bidirectional optical scanner comprising:
 a compression module having a first compression plate and a second compression plate,
 a first optical detection module disposed over the first compression plate; the first optical detection module having at least one light source module and at least one detection module; the light source module including a plurality of light emitting elements arranged in a line; the detection module having a plurality of photosensors disposed in a line; the detection module having a plurality of photosensors disposed in a line; one of the light emitting elements aligned with the corresponding photosensor to form a row; and
 a second optical detection module arranged under the second compression plate; the second optical detection module including at least one light source module and at least one detection module; the light source module having a plurality of light emitting elements arranged in a line and the detection module having a plurality of photosensors disposed in a line; one of the light emitting elements aligned with the corresponding photosensor to form a row; the light emitting elements of the light source module of the second optical detection module are corresponding to the photosensors of the detection module of the first optical detection module; the photosensors of the detection module of the second optical detection module are corresponding to the light emitting elements of the light source module of the first optical detection module.

2. The device as claimed in claim 1, wherein the light emitting element is an optical fiber that emits laser light or broadband light.

3. The device as claimed in claim 2, wherein wavelength of the laser light or of the broadband light is near infrared wavelength.

4. The device as claimed in claim 1, wherein the bidirectional optical scanner further includes a moving platform that is disposed with the first optical detection module.

5. The device as claimed in claim 4, wherein the moving platform includes:
a first moving platform that is arranged with the first optical detection module; and
a second moving platform that is arranged with the first moving platform, located over and perpendicular to the first moving platform.

6. The device as claimed in claim 5, wherein the first moving platform includes:
a first base;
a threaded rod that is disposed on the base and is arranged with the first optical detection module; and
a driving device that is disposed on the first base and is connected to the threaded rod.

7. The device as claimed in claim 6, wherein the first optical detection module further includes:
a fastener having a first fixed end and a second fixed end; the light emitting elements of the light source module and the photosensors of the detection module are fixed on the first fixed end while the second fixed end is screwed on the threaded rod of the first moving platform.

8. The device as claimed in claim 6, wherein the driving device is a servo motor.

9. The device as claimed in claim 6, wherein the second moving platform includes:
a second base connected to the first base of the first moving platform;
a first threaded rod disposed on one side of the second base;
a second threaded rod disposed on the other side of the second base; and
a driving device that is arranged at the second base and is connected to the first threaded rod.

10. The device as claimed in claim 9, wherein the first moving platform further includes:
two connection parts disposed on two ends of the first base; one of the two connection parts is screwed on the first threaded rod while the other connection part is screwed on the second threaded rod.

11. The device as claimed in claim 9, wherein the driving device is a servo motor.

12. The device as claimed in claim 4, wherein the bidirectional optical scanner further includes:
a frame for fixing both the moving platform and the first compression plate.

13. The device as claimed in claim 12, wherein the bidirectional optical scanner further includes:
a third moving platform disposed on the frame.

14. The device as claimed in claim 13, wherein the third moving platform includes:
a third base;
a threaded rod that is disposed on the third base and is screwed with the frame; and
a driving device connected to the threaded rod.

15. The device as claimed in claim 14, wherein the driving device is a servo motor.

16. The device as claimed in claim 1, wherein the bidirectional optical scanner further includes a moving platform that is disposed with the second optical detection module.

17. The device as claimed in claim 16, wherein the moving platform includes:
a first moving platform that is arranged with the second optical detection module; and
a second moving platform that is arranged with the first moving platform, located under and perpendicular to the first moving platform.

18. The device as claimed in claim 17, wherein the first moving platform includes:
a base;
a threaded rod that is disposed on the base and is arranged with the second optical detection module; and
a driving device that is arranged at the base and is connected to the threaded rod.

19. The device as claimed in claim 18, wherein the first optical detection module further includes:
a fastener having a first fixed end and a second fixed end; the light emitting elements of the light source module and the photosensors of the detection module are fixed on the first fixed end while the second fixed end is screwed on the threaded rod of the first moving platform.

20. The device as claimed in claim 18, wherein the driving device is a servo motor.

21. The device as claimed in claim 17, wherein the second moving platform includes:
a fourth base connected to the first base of the first moving platform;
a fourth base connected to the first base of the first moving platform;
a first threaded rod disposed on one side of the base;
a second threaded rod disposed on the other side of the base;
a driving device that is disposed on the fourth base and is connected to the first threaded rod.

22. The device as claimed in claim 17, wherein the second moving platform includes:
two connection parts disposed on two ends of the fourth base; one of the two connection parts is screwed on the first threaded rod while the other connection part is screwed on the second threaded rod.

23. The device as claimed in claim 21, wherein the driving device is a servo motor.

* * * * *